(12) United States Patent
Mason et al.

(10) Patent No.: US 7,937,129 B2
(45) Date of Patent: May 3, 2011

(54) VARIABLE APERTURE SENSOR

(75) Inventors: Eugene Mason, La Habra Hts, CA (US); Brian Volken, Mission Viejo, CA (US)

(73) Assignee: MASIMO Corporation, Irvine, CA (US)

( * ) Notice: Subject to any disclaimer, the term of this patent is extended or adjusted under 35 U.S.C. 154(b) by 1317 days.

(21) Appl. No.: 11/386,076

(22) Filed: Mar. 21, 2006

(65) Prior Publication Data

US 2006/0258922 A1 Nov. 16, 2006

Related U.S. Application Data

(60) Provisional application No. 60/663,952, filed on Mar. 21, 2005.

(51) Int. Cl.
*A61B 5/1455* (2006.01)
(52) U.S. Cl. .......................... 600/323; 600/344; 600/310
(58) Field of Classification Search .................. 600/323, 600/344
See application file for complete search history.

(56) References Cited

U.S. PATENT DOCUMENTS

| | | | |
|---|---|---|---|
| 4,223,228 A * | 9/1980 | Kaplan | 378/205 |
| 4,907,876 A * | 3/1990 | Suzuki et al. | 356/41 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| D353,195 S | 12/1994 | Savage et al. | |
| D353,196 S | 12/1994 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |

(Continued)

*Primary Examiner* — Eric F Winakur
(74) *Attorney, Agent, or Firm* — Knobbe Martens Olson & Bear LLP

(57) ABSTRACT

A variable aperture sensor has a first jaw and a second jaw that are rotatably attached. An emitter is disposed in the first jaw, and a detector is disposed in the second jaw. The jaws are adapted to attach to a tissue site so that the emitter transmits optical radiation into the tissue site and the detector receives optical radiation through a variable aperture after absorption by the tissue site. The variable aperture is disposed in the second jaw and configured to adjust the amount of the optical radiation received by the detector.

14 Claims, 7 Drawing Sheets

U.S. PATENT DOCUMENTS

| | | |
|---|---|---|
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,014,204 A * | 1/2000 | Prahl et al. ............ 356/73 |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,621 A * | 9/2000 | Chin ............ 600/323 |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,895 B1 * | 9/2001 | Ristolainen et al. ......... 600/323 |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 2002/0039184 A1 * | 4/2002 | Sandusky ............ 356/369 |
| 2005/0110986 A1 * | 5/2005 | Nikoonahad et al. ...... 356/237.2 |

* cited by examiner

VARIABLE APERTURE SENSOR

REFERENCE TO RELATED APPLICATION

The present application claims priority benefit under 35 U.S.C. §119(e) from U.S. Provisional Application No. 60/663,952, filed Mar. 21, 2005, entitled "Variable Aperture Sensor." The present application incorporates the foregoing disclosure herein by reference.

BACKGROUND OF THE INVENTION

Pulse oximeters are noninvasive, easy to use, inexpensive instruments for measuring the oxygen saturation level of arterial blood. Pulse oximeters reduce the risk of accidental death and injury by providing early detection of decreases in the arterial oxygen supply. As a result, pulse oximeters have gained rapid acceptance in a wide variety of medical applications, including surgical wards, intensive care units, general wards and home care. These instruments perform a spectral analysis of the pulsatile component of arterial blood so as to determine the relative concentration of oxygenated hemoglobin, the major oxygen carrying constituent of blood.

FIG. 1 illustrates a pulse oximetry sensor 100 having emitters 110, a detector 120, and an aperture 130. The sensor 100 is attached to a patient at a selected tissue site 10, such as a fingertip or ear lobe. The emitters 110 are positioned to project light through the blood vessels and capillaries of the tissue site 10, and the detector 120 is positioned so as to detect the emitted light as it emerges from the tissue site 10. The aperture 130 allows emitter generated light that is transmitted through and partially absorbed by the tissue site 10 to reach the detector 120, while excluding ambient light and other noise sources. A pulse oximetry sensor is described in U.S. Pat. No. 6,088,607 entitled "Low Noise Optical Probe," which is assigned to Masimo Corporation, Irvine, Calif. and incorporated by reference herein.

FIG. 2 illustrates a pulse oximetry system 200 having a monitor 201 and a sensor 100. The monitor 201 has drivers 210, a controller 220, a front-end 230, a signal processor 240 and a display 250. The drivers 210 alternately activate the emitters 110 as determined by the controller 220. The front-end 230 conditions and digitizes the resulting current generated by the detector 120, which is proportional to the intensity of the detected light. The signal processor 240 inputs the conditioned detector signal and determines oxygen saturation along with pulse rate. The display 250 provides a numerical readout of a patient's oxygen saturation and pulse rate. A pulse oximetry monitor is described in U.S. Pat. No. 5,482,036 entitled "Signal Processing Apparatus and Method," which is assigned to Masimo Corporation, Irvine, Calif. and incorporated by reference herein.

SUMMARY OF THE INVENTION

FIG. 3 is a graph 300 illustrating a detector characteristic curve 310, which is plotted as detector output current 302 verses light intensity 301 incident on the detector 120 (FIG. 1). The characteristic curve 310 has a linear region 312 and a saturation region 314. The linear region 312 corresponds to incident intensity 301 less than a saturation intensity $I_{sat}$ 316 and a resulting output current less than a saturation current $i_{sat}$ 317. Ideally, the detector has an operating point 318 in the linear region 312. To provide sufficient detector dynamic range, the operating point 318 is ideally positioned away from the detector saturation current $i_{sat}$ 317 and the detector dark current $i_{dark}$ 319 at either extreme of the linear region 312.

Tissue site thickness and opacity vary significantly from patient to patient and between tissue sites. For example, light absorption is significantly different for a finger site as compared with an ear lobe site. Variation is tissue site characteristics results in a large variation of incident light intensity 301 on the detector for a given emitted light intensity. Some of this variation can be accommodated by adjusting the drive current to the emitters 110 (FIG. 2) and controlling the gain at the front-end 230 (FIG. 2). A variable aperture sensor, however, advantageously provides a mechanical means of adjusting the incident light intensity 301 so as to accommodate tissue site variation and control the detector operating point 318.

One aspect of a variable aperture sensor comprises a first jaw and a second jaw that are rotatably attached. An emitter is disposed in the first jaw, and a detector is disposed in the second jaw. The jaws are adapted to attach to a tissue site so that the emitter transmits optical radiation into the tissue site and the detector receives optical radiation through a variable aperture after absorption by the tissue site. The variable aperture is disposed in the second jaw and configured to adjust the amount of the optical radiation received by the detector.

In one embodiment, the variable aperture has a fixed aperture defined by the second jaw and a slide movable between a wide open position and a stopped down position. The wide open position is adapted to pass maximal optical radiation to the detector. The stopped down position is adapted to pass minimal optical radiation to the detector. An open portion is defined by the slide and generally aligned with the fixed aperture in the open position and a light block portion of the slide is generally aligned with the fixed aperture in the stopped down position.

In another embodiment, the variable aperture has a fixed aperture defined by the second jaw and a shutter installed within the fixed aperture. The shutter is movable between a wide open position and a stopped down position. The wide open position is adapted to pass maximal optical radiation to the detector. The stopped down position is adapted to pass minimal optical radiation to the detector.

Another aspect of a variable aperture sensor is a method having the steps of emitting optical radiation into a tissue site and attenuating the optical radiation after absorption by the tissue site. Additional steps include detecting the optical radiation after absorption by the tissue site and generating a physiological signal responsive to the absorption. In one embodiment, the attenuating step comprises the substep of varying an aperture size so as to compensate for tissue site physical and physiological characteristics. In a particular embodiment, the varying substep comprises the substep of altering a shutter opening within a fixed aperture. In another particular embodiment, the varying substep comprises the substep of sliding a light block across a fixed aperture.

A further aspect of a variable aperture sensor comprises an emitter means for transmitting optical radiation into a tissue site and a detector means for receiving the optical radiation after absorption by the tissue site. An attachment means is for positioning the emitter means and the detector means on the tissue site and an attenuating means is disposed in the attachment means for reducing the optical radiation incident on the detector means. In one embodiment, the attenuating means includes a fixed aperture means for passing the optical radiation between the tissue site and the detector means, and a stopping down means for variably reducing the fixed aperture means. In a particular embodiment, the stopping down means has a sliding light block means for covering a portion of the fixed aperture means. In another particular embodiment, the stopping down means has a shutter means for reducing the opening of the fixed aperture means.

DETAILED DESCRIPTION OF THE PREFERRED EMBODIMENTS

Figure 1:
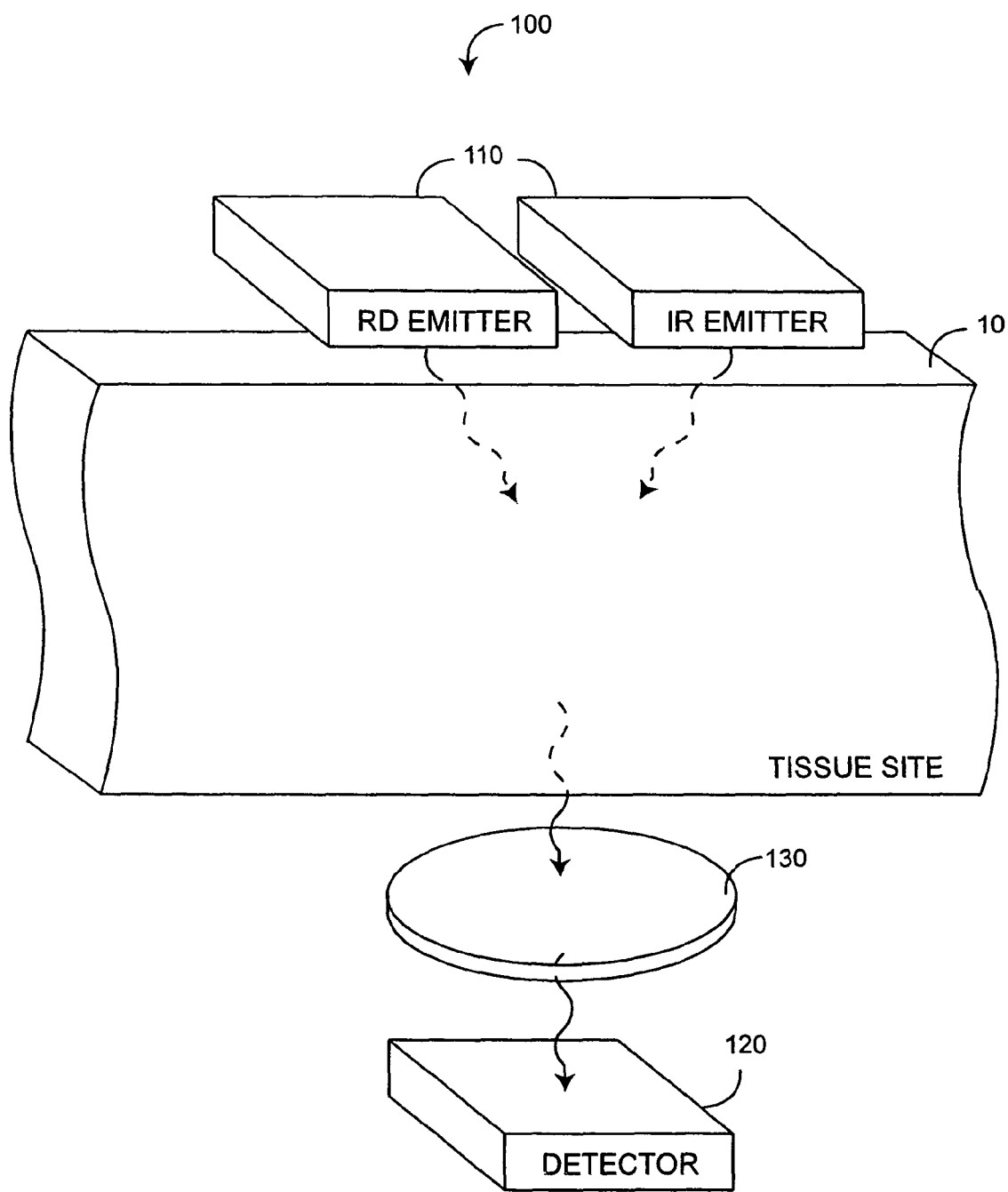
FIG. 1 is an illustration of a prior art sensor.
Figure 2:
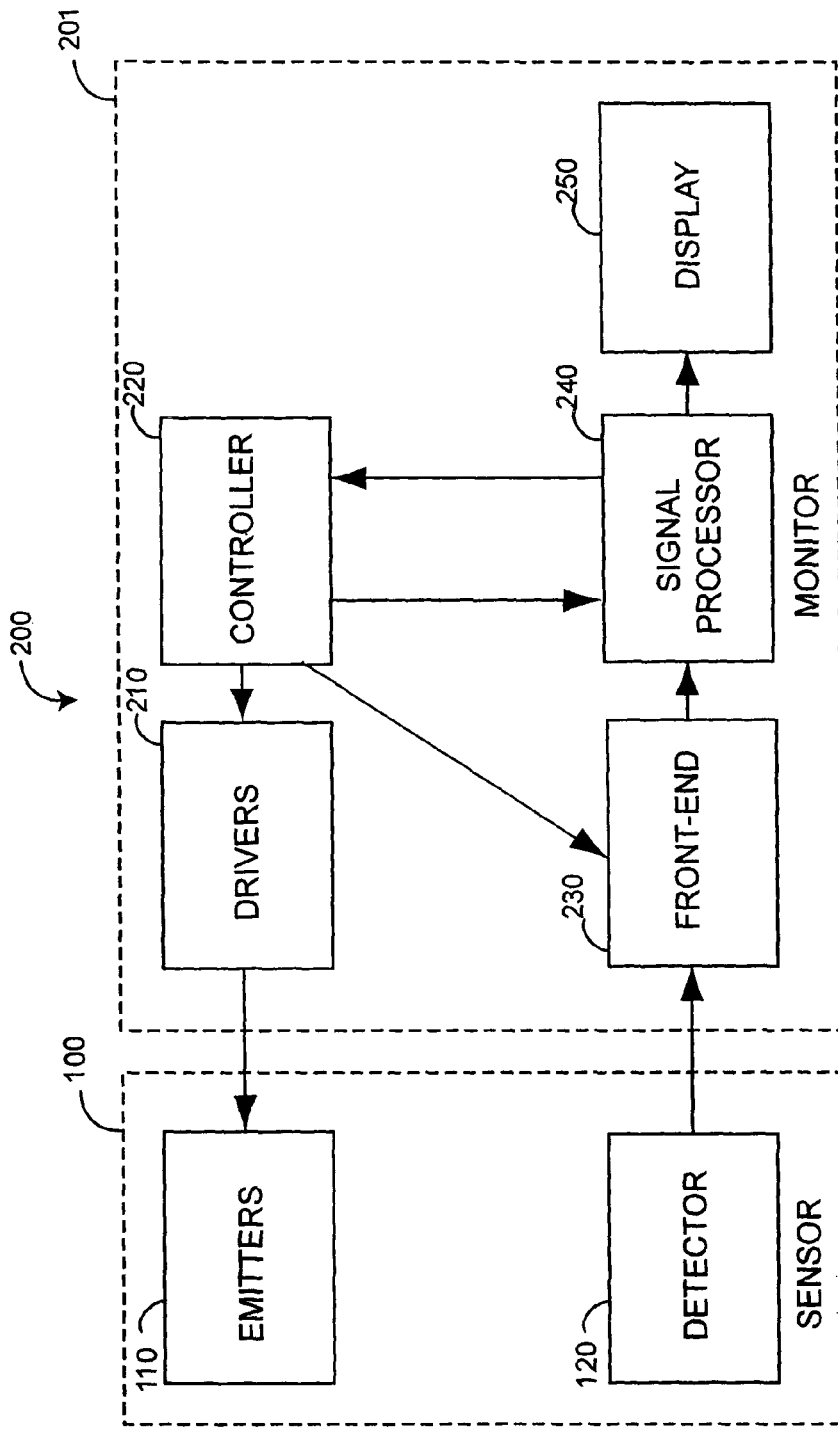
FIG. 2 is a block diagram of a prior art pulse oximetry system.
Figure 3:
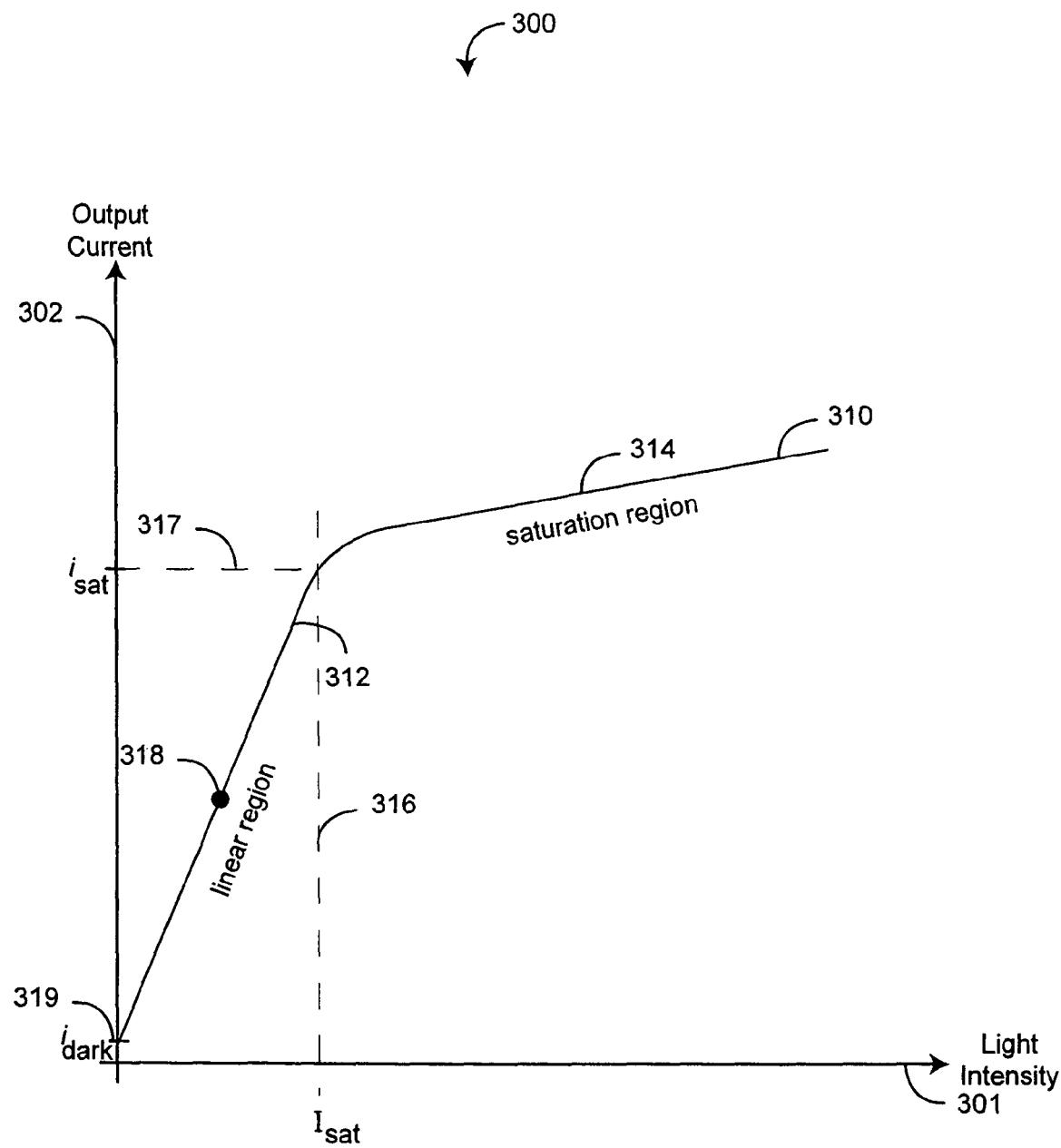
FIG. 3 is a graph of detector output current versus incident light intensity.
Figure 4:
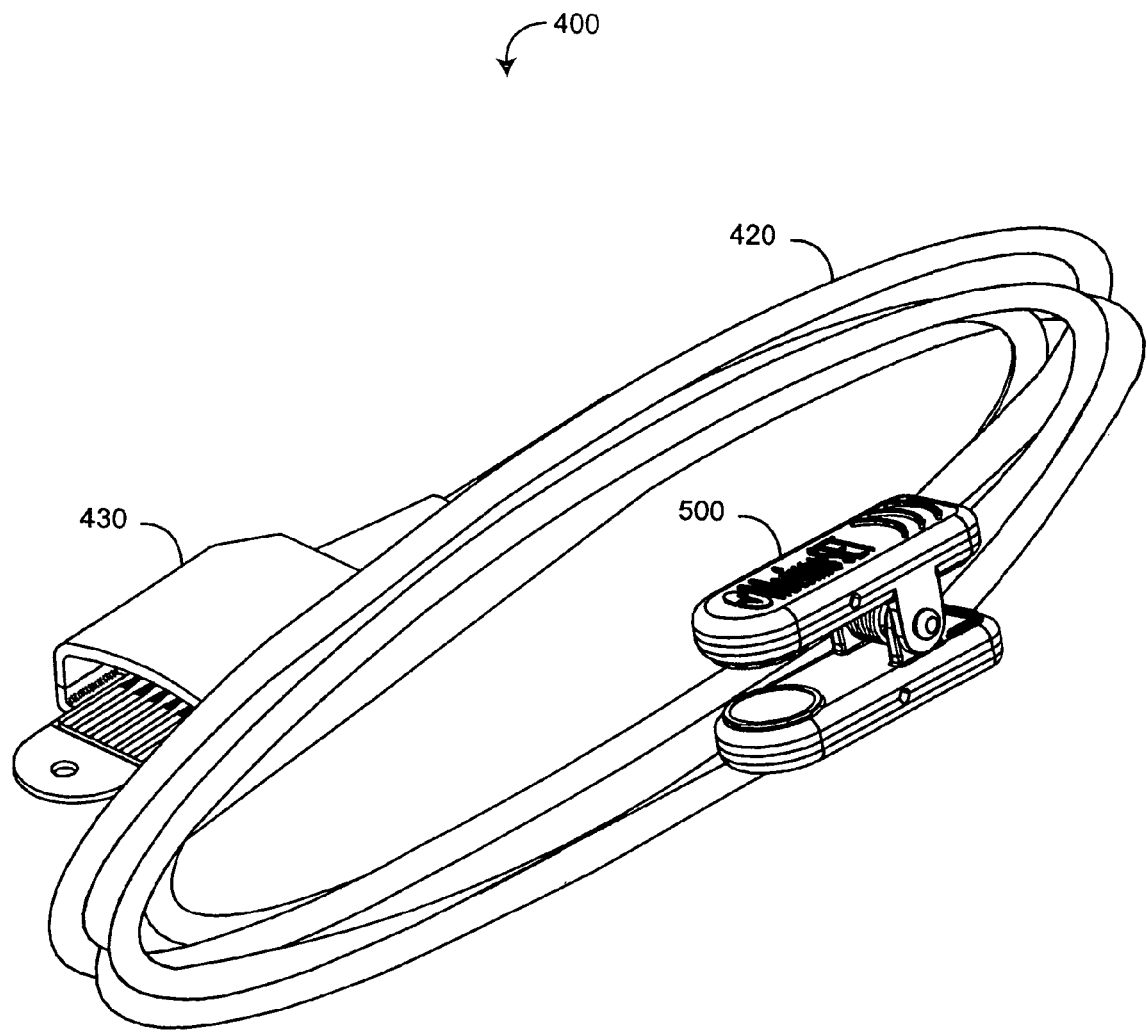
FIG. 4 is a perspective view of a reusable sensor.

FIG. 4 illustrates a reusable sensor 400 having a sensor body 500, a cable 420 and a connector 430. The sensor body 500 houses emitters 510 (FIG. 5), a detector 520 (FIG. 5) and a variable aperture 530 (FIG. 5), as described in detail with respect to FIG. 5. The cable 420 provides electrical communication between the emitters 510 (FIG. 5), the detector 520 and the connector 430. The connector 430 is adapted to a patient cable, which provides electrical communication between the sensor 400 and a monitor (not shown).

Figure 5:
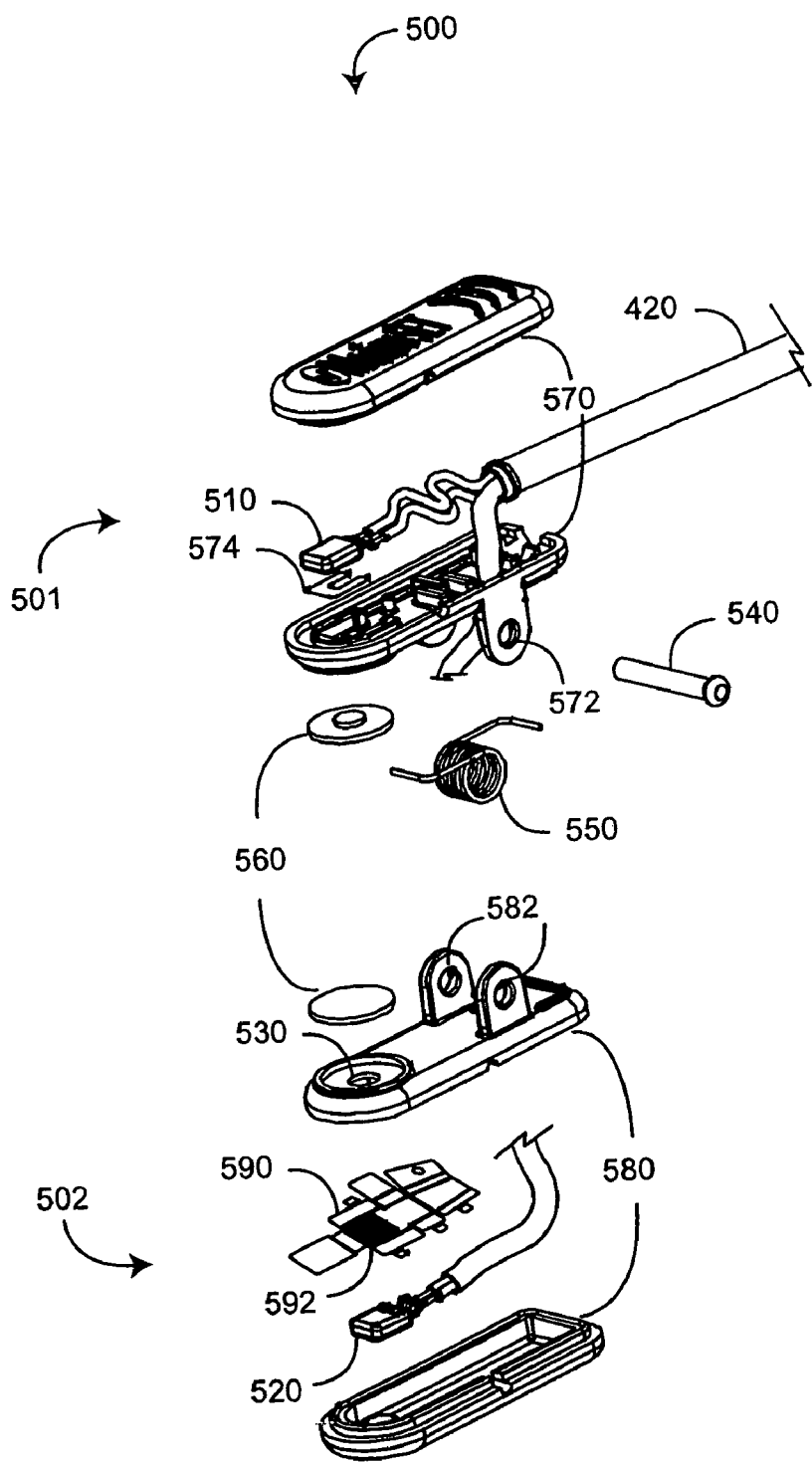
FIG. 5 is an exploded perspective view of a sensor body.

FIG. 5 further illustrates a sensor body 500 having a top jaw 501 and a bottom jaw 502. The jaws 501, 502 are rotatably attached around a hinge pin 540 inserted through hinges 572, 582 so as to retain a spring 550. The spring 550 urges the jaws 501, 502 to a closed position in which optically transparent pads 560 are held against a tissue site. The top jaw 501 has a top shell 570 that houses the emitters 510, which are held in place with pressure sensitive adhesive (PSA) 574. The bottom jaw 502 has a bottom shell 580 that houses the detector 520, which is enclosed in an EMI shield 590 and held in place with PSA (not shown). Light passes from the emitters 510 through the variable aperture 530 to the detector 520. Embodiments of the variable aperture are described with respect to FIGS. 6-7, below.

Figures 6A, 6B:
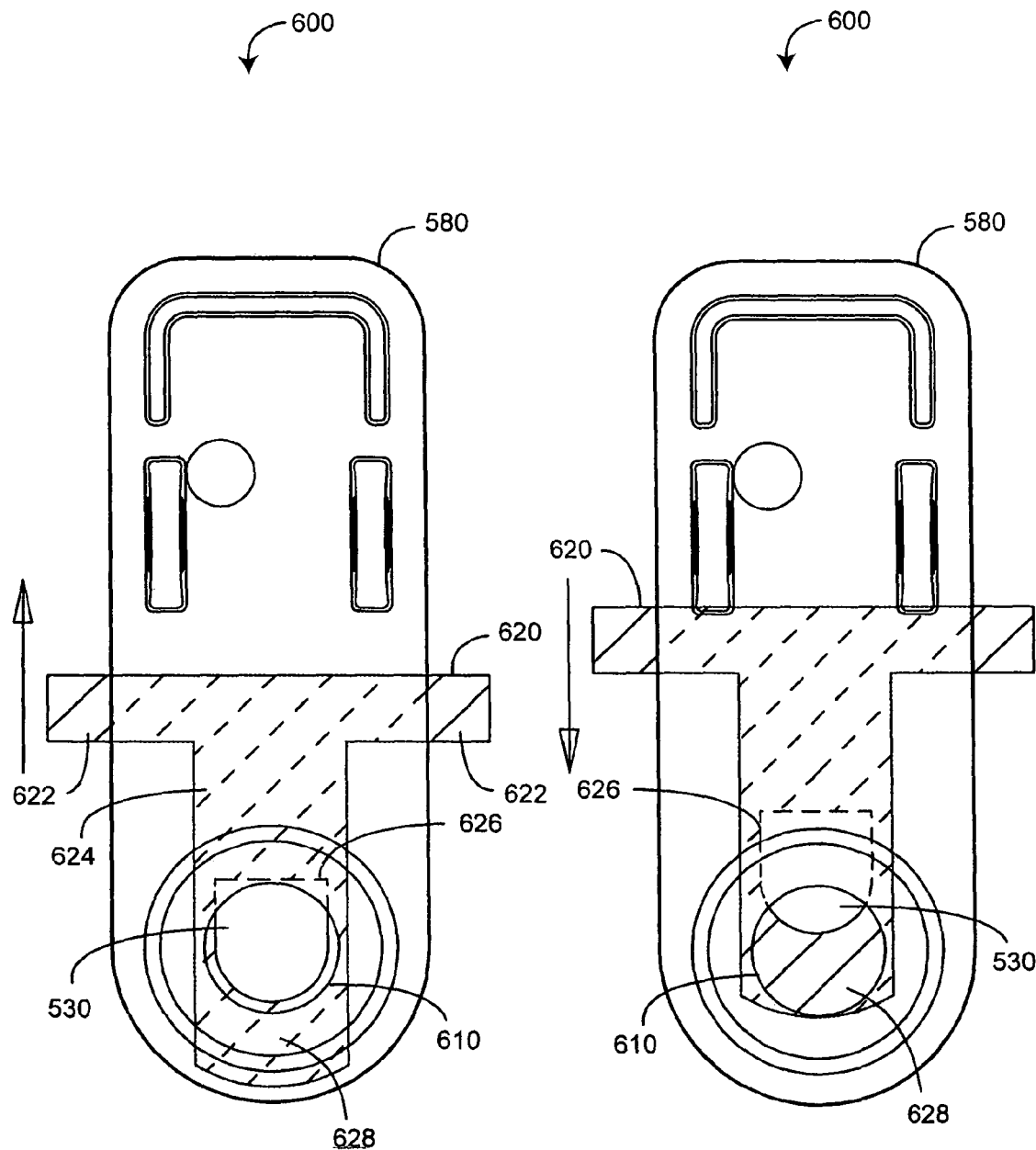
FIGS. 6A-B are top plan views of a slide actuated variable aperture sensor.

FIGS. 6A-B illustrate a slide actuated variable aperture sensor 600. The bottom jaw 580 has a variable aperture 530 adjustable between wide-open (FIG. 6A) so as to pass a maximum amount of light to the detector and stopped-down (FIG. 6B) so as to pass a minimum amount of light. In particular, the variable aperture 530 comprises a fixed aperture 610 defined by the bottom jaw 580 and a slide 620. The slide 620 is slideably mounted within the bottom jaw 580 so as to overlap the fixed aperture 610. The slide 620 is generally T-shaped having arms 622 and a leg 624. The leg 624 defines an open portion 626 and a light block portion 628. The arms 622 extend from the sides of the bottom jaw 580 to form a grip so that the slide 620 can be manually positioned relative to the bottom jaw 580. The slide 620 is movable between a first position (FIG. 6A) corresponding to a wide-open variable aperture 530, where the open portion 626 is generally aligned with the fixed aperture 610, and a second position (FIG. 6B) corresponding to a stopped-down variable aperture 530, where the light block portion 628 is generally aligned with the fixed aperture 610.

Figure 7A:
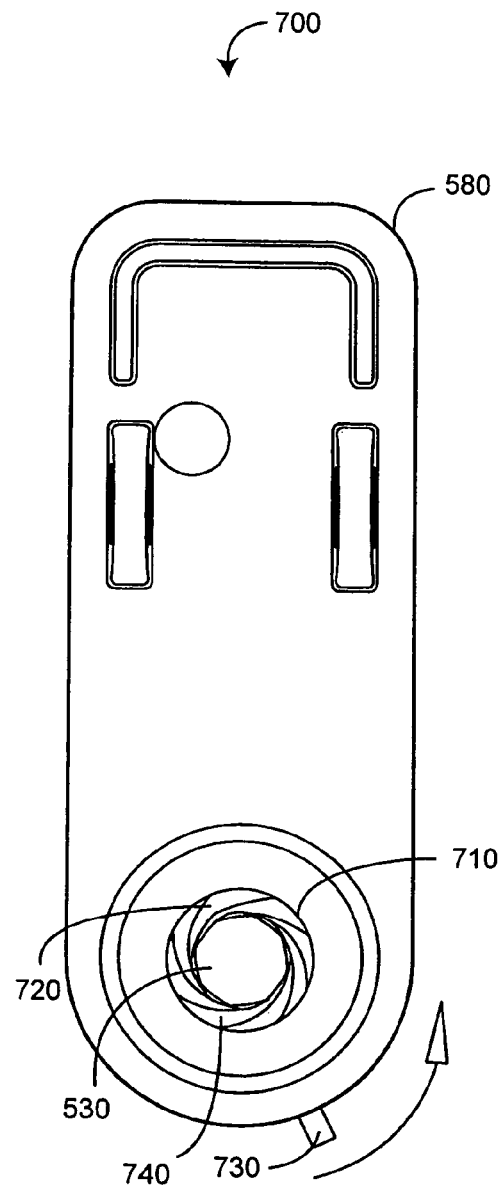
FIGS. 7A-B are top plan views of a shutter actuated variable aperture sensor.
Figure 7B:
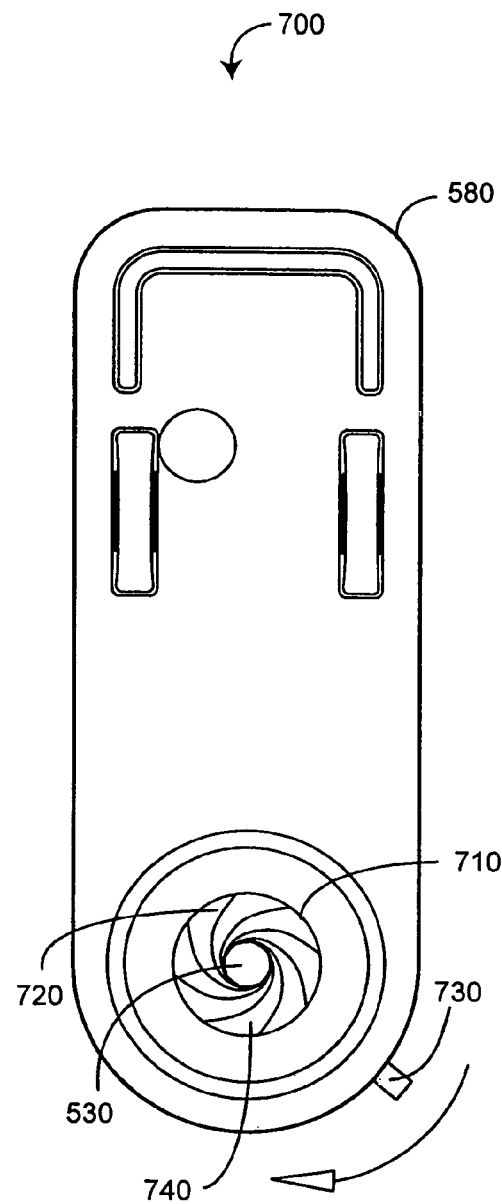

FIGS. 7A-B illustrate a shutter actuated variable aperture sensor 700. The bottom jaw 580 has a variable aperture 530 adjustable between wide-open (FIG. 7A) so as to pass a maximum amount of light to the detector and stopped-down (FIG. 7B) so as to pass a minimum amount of light. In particular, the variable aperture 530 comprises a fixed aperture 710 defined by the bottom jaw 580 and a shutter 720 installed within the fixed aperture 710. A lever 730 is connected to and adapted to position multiple overlapping leaves 740 so as to control the shutter 720. In particular, the lever 730 extends from the bottom jaw 580 and is manually movable between a first position (FIG. 7A) corresponding to a wide-open variable aperture 530 and a second position (FIG. 7B) corresponding to a stopped-down variable aperture 530.

A variable aperture sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A pulse oximetry sensor comprising:
    a first jaw;
    an emitter disposed in said first jaw;
    a second jaw rotatably attached to said first jaw;
    a detector disposed in said second jaw; and
    a variable aperture disposed in said second jaw,
    said jaws adapted to attach to a tissue site so that said emitter transmits optical radiation into said tissue site and said detector receives optical radiation through said variable aperture after absorption by said tissue site,
    said variable aperture configured to adjust the amount of said optical radiation received by said detector.

2. The pulse oximetry sensor according to claim 1 wherein said variable aperture comprises:
    a fixed aperture defined by said second jaw;
    a slide movable between a wide open position and a stopped down position, said wide open position adapted to pass maximal optical radiation to said detector, said stopped down position adapted to pass minimal optical radiation to said detector;
    an open portion defined by said slide and generally aligned with said fixed aperture in said open position; and
    a light block portion of said slide generally aligned with said fixed aperture in said stopped down position.

3. The pulse oximetry sensor according to claim 2 wherein said slide comprises:
    a grip adapted for manually positions said slide; and
    an extension extending from said grip and overlapping with said fixed aperture.

4. The pulse oximetry sensor according to claim 1 wherein said variable aperture comprises:
    a fixed aperture defined by second jaw; and
    a shutter installed within said fixed aperture,
    said shutter movable between a wide open position and a stopped down position,
    said wide open position adapted to pass maximal optical radiation to said detector, said stopped down position adapted to pass minimal optical radiation to said detector.

5. The pulse oximetry sensor according to claim 4 wherein said shutter comprises:
    a lever; and
    a plurality of leaves disposed within said fixed aperture,
    said lever configured to position said leaves, said lever adapted to manually move between a first position corresponding to said open position and a second position corresponding to said stopped down position.

6. The pulse oximetry sensor according to claim 1, wherein said variable aperture is configured to receive manual adjustment of the amount of said optical radiation received by said detector.

7. A pulse oximetry sensor method comprising the steps of:
    emitting optical radiation into a tissue site from a first jaw of a housing;

manually varying a size of an aperture, said size responsive to tissue site physical and physiological characteristics, said manual varying adjusting attenuation of said optical radiation;

detecting, at a second jaw of said housing hingably attached to said first jaw, said optical radiation that has passed through said aperture and been absorbed by said tissue site; and generating a physiological signal responsive to said absorption.

8. A pulse oximetry sensor method according to claim 7 wherein said manually varying a size of said aperture comprises manually varying a size of a fixed aperture.

9. A pulse oximetry sensor method according to claim 8 wherein said manually varying comprises altering a shutter opening within said fixed aperture.

10. A pulse oximetry sensor method according to claim 8 wherein said manually varying comprises sliding a light block across said fixed aperture.

11. A pulse oximetry sensor comprising:

means for transmitting optical radiation into a tissue site;

means for receiving said optical radiation after absorption by said tissue site;

means for positioning said means for transmitting and said means for receiving on said tissue site including a clam shell housing configured to substantially close around said tissue site; and an intensity adjuster for manually adjusting an intensity of said optical radiation incident on said means for receiving, said intensity adjuster comprising one or more devices configured to vary a size of an aperture through which said optical radiation passes.

12. The pulse oximetry sensor according to claim 11 wherein said aperture comprises a fixed aperture and said intensity adjuster comprises:

means for passing said optical radiation between said tissue site and said means for receiving; and means for variably reducing said fixed aperture means.

13. The pulse oximetry sensor according to claim 12 wherein said means for variably reducing comprises a sliding light block that covers a portion of said fixed aperture.

14. The pulse oximetry sensor according to claim 12 wherein said means for variably reducing comprises a shutter that reduces an opening of said fixed aperture.

* * * * *

UNITED STATES PATENT AND TRADEMARK OFFICE
CERTIFICATE OF CORRECTION

| | |
|---|---|
| PATENT NO. | : 7,937,129 B2 |
| APPLICATION NO. | : 11/386076 |
| DATED | : May 3, 2011 |
| INVENTOR(S) | : Eugene Mason and Brian Volken |

It is certified that error appears in the above-identified patent and that said Letters Patent is hereby corrected as shown below:

* Column 6, Line 15, in Claim 12, change "aperture means." to --aperture.--.

Signed and Sealed this
Twenty-ninth Day of November, 2011

David J. Kappos
*Director of the United States Patent and Trademark Office*